(12) United States Patent
Chatterjee et al.

(10) Patent No.: US 8,148,302 B2
(45) Date of Patent: Apr. 3, 2012

(54) IN SITU ASSEMBLING OF PROTEIN MICROARRAYS

(75) Inventors: Deb K Chatterjee, Potomac, MD (US); Kalavathy Sitaraman, Frederick, MD (US); James L Hartley, Frederick, MD (US); Cassio Baptista, Frederick, MD (US); David J Munroe, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 521 days.

(21) Appl. No.: 11/252,735

(22) Filed: Oct. 19, 2005

(65) Prior Publication Data

US 2007/0087356 A1 Apr. 19, 2007

(51) Int. Cl.
*C40B 40/08* (2006.01)
*C12N 15/63* (2006.01)

(52) U.S. Cl. ..................... 506/17; 435/320.1
(58) Field of Classification Search ................. None
See application file for complete search history.

(56) References Cited

U.S. PATENT DOCUMENTS

| 5,270,163 | A | 12/1993 | Gold et al. | |
|---|---|---|---|---|
| 2003/0176644 | A1 | 9/2003 | Byrd et al. | |
| 2005/0260653 | A1 | 11/2005 | Labaer et al. | |
| 2007/0184451 | A1* | 8/2007 | Byrd et al. | 435/6 |

FOREIGN PATENT DOCUMENTS

| WO | WO 02/14860 | 2/2002 |
|---|---|---|
| WO | WO 02/062957 A2 | 8/2002 |
| WO | WO 03/010176 A2 | 2/2003 |

OTHER PUBLICATIONS

Bell et al. The Lac repressor: a second generation of structural and functional studies. Curr. Opin. in Struct. Biol. 11: 19-25, 2001.*
You et al. The conformational properties of DNA lesions such as extrahelical bulges are presumed to be essential for recognition of defeBiophys. J.: Biophys Letters L43-L45, 2005.*
Bidnenko et al. Replication fork collapse at replication terminator sequences. EMBO 21(14): 3898-3907, 2002.*
Neylon et al. Replication termination in *Escherichia coli*: structure and antihelicase activity of the Tus-Ter complex. Micro. ad Mol. Biol. Rev. 69(3): 501-526, 2005.*
Merten et al. Tight Transcriptional Control Mechanism Ensures Stable High-Level Expression from T7 Promoter-Based Expression Plasmids. Nature Biotechnology 13, 175-179 (1995).*
Büssow et al., Abstract: *Nucleic Acids Research*, vol. 26 (No. 21), 5007-5008 (1998).
Fletcher et al., *Journal of Nanobiotechnology*,UK, vol. 1, 16p (2003).
LaBaer et al., *Current Opinion in Chemical Biology*, 9(1), 14-19 (2005).
Vidal et al., *Nucleic Acids Research*, 27(4), 919-929 (1999).
Cahill et al., *Adv. Biochem. Eng. Biotechnol.*, 83: 177 (2003).
Haab et al., *Genome Biology*, 2(2) 0004.1-0004.13 (2001).
He et al., *Nucleic Acids Res.*, 29 (e73), 1-6 (2001).
He, *Methods in Molecular Biology*, 264,25-31 (2004).
Jona et al., *Curr. Opin. Mol. Ther.*, 5: 271 (2003).
Lueking et al., *Anal. Biochem.*, 270: 103 (1999).
MacBeath et al., *Science*, 289: 1760 (2000).
Newman et al., *Science*, 300: 2097 (2003).
Nord et al., *J. Biotech.*, 106: 1-13 (2003).
Ramachandran et al.,*Science*, 305, 86-90 (2004).
Zhu et al., *Science*, 293: 2101 (2001).
Choi et al., *Biochemical and Biophysical Research Communications*, 329, 1315-1319 (2005).

* cited by examiner

*Primary Examiner* — Michele K Joike
(74) *Attorney, Agent, or Firm* — Leydig, Voit & Mayer

(57) ABSTRACT

The invention provides a microarray and methods for producing a protein microarray. The array comprises multiple nucleic acid molecules immobilized on a substrate, each comprising (i) a protein-binding domain and (ii) a nucleic acid sequence encoding a fusion protein comprising a polypeptide of interest and a DNA-binding protein that binds the protein-binding domain, and one or more fusion proteins produced from the multiple nucleic acid molecules. Each fusion protein is immobilized on the substrate via binding to a nucleic acid sequence comprising the protein-binding domain present on the nucleic acid molecule from which the fusion protein is produced or on the substrate. The invention also provides a method of analyzing protein interactions with, for example, other proteins, lipids and drugs.

12 Claims, 4 Drawing Sheets

IN SITU ASSEMBLING OF PROTEIN MICROARRAYS

BACKGROUND OF THE INVENTION

Protein microarrays provide a powerful tool for the study of protein function and protein-protein interactions. In particular, protein microarrays have been used to investigate protein interaction with various drugs, antibodies, lipids, nucleic acids, and other proteins. Protein microarrays currently are available in two general formats: antibody arrays and target protein arrays. Antibody arrays contain an array of antibodies that measure the abundance of specific proteins in samples (see, e.g., Haab et al., *Genome Biology*, 2: research004.1-0004.13 (2001). Target protein arrays, on the other hand, contain an array of proteins of interest that are used to measure the abundance of proteins in response to specific exogenous stimuli (e.g., drugs, antibodies, lipids, etc.), or to identify enzyme substrates (see, e.g., Cahill et al., *Adv. Biochem. Eng. Biotechnol.*, 83: 177 (2003) and Jona et al., *Curr. Opin. Mol. Ther.*, 5: 271 (2003)).

Target protein microarrays typically are generated in two steps. First, proteins are separately produced, and then applied (or "spotted") on the array surface using a variety of linkage chemistries (see, e.g., Lueking et al., *Anal. Biochem.*, 270: 103 (1999), MacBeath et al., *Science*, 289: 1760 (2000), Zhu et al., *Science*, 293: 2101 (2001), and Newman et al., *Science*, 300: 2097 (2003)). Despite their demonstrated utility, the widespread use of target protein microarrays has been limited by a number of factors. For example, current protein microarray technologies are labor-intensive. In addition, currently there are no high-throughput expression systems that produce significant yields of mammalian proteins of sufficiently high purity. Moreover, protein instability, both before and after spotting on the array, is another obstacle to the implementation of target protein microarrays on a large-scale.

To circumvent the problems associated with current protein microarray technology, researchers have developed new systems in which immobilized DNA molecules are transcribed and translated on the microarray in situ, whereupon newly synthesized proteins are immobilized on the microarray surface at the site of expression. For example, Nord et al., *J Biotech.*, 106: 1-13 (2003) discloses an array technology called microbead display of proteins. In this technology, proteins are captured by antigen-antibody binding as they are synthesized. Specifically, biotin labeled PCR products (containing a bacteriophage T7 promoter and a FLAG epitope in-frame with two IgG binding domains) are first anchored onto microbeads through streptavidin-biotin affinity binding. Anti-FLAG antibody also is immobilized onto the same microbead. The beads are then incubated with a coupled cell-free transcription-translation extract to produce the corresponding protein. The newly synthesized proteins are trapped via FLAG peptide-FLAG antibody interaction. In addition, Ramachandran et al., *Science*, 305: 86-90 (2004), discloses a similar antibody-mediated protein microarray format. In this case, purified plasmids are arrayed on a microscope slide through biotin-avidin binding. The genes encoded by the plasmids are fused with glutathione-S-transferase (GST) protein to produce GST-fusion proteins. The slides also are printed with polyclonal GST antibody to capture the newly synthesized GST-fusion proteins following coupled cell-free transcription-translation reactions. Other methods for generating protein microarrays utilizing direct immobilization of proteins synthesized in situ are disclosed in, for example, He, *Methods in Molecular Biology*, 264: 25-31 (2004) and International Patent Application Publication WO 02/14860.

While the above methods have met with some success, their widespread use is limited by a number of factors. First, both methods require a second protein, i.e., an antibody, to capture the synthesized protein of interest. Antibody generation and purification adds time and cost to the process. Second, methods for maintaining long-term antibody stability, and therefore, array stability, have yet to be developed.

Accordingly, there remains a need for more robust and stable protein microarrays and more efficient methods for producing such protein microarrays. The invention provides such microarrays and methods. These and other advantages of the invention, as well as additional inventive features, will be apparent from the description of the invention provided herein.

BRIEF SUMMARY OF THE INVENTION

The invention provides a microarray comprising (a) a substrate, (b) multiple nucleic acid molecules immobilized on the substrate, wherein each nucleic acid molecule comprises (i) a protein-binding domain and (ii) a nucleic acid sequence encoding a fusion protein comprising a polypeptide of interest and a DNA-binding protein, and (c) one or more fusion proteins produced from the multiple nucleic acid molecules, wherein each fusion protein is immobilized on the substrate via binding to the protein-binding domain on the nucleic acid molecule.

The invention also provides methods for producing a protein microarray. In one embodiment, the method comprises (a) preparing multiple nucleic acid molecules, wherein each nucleic acid molecule comprises (i) a protein-binding domain and (ii) a nucleic acid sequence encoding a fusion protein comprising a polypeptide of interest and a DNA-binding protein, (b) contacting a substrate with the multiple nucleic acid molecules, (c) immobilizing the multiple nucleic acid molecules on the substrate, (d) contacting the immobilized nucleic acid molecules with an expression composition, wherein the nucleic acid sequence encoding the fusion protein is expressed and the fusion protein is produced, whereupon each fusion protein is immobilized on the substrate via binding to the protein-binding domain on the nucleic acid molecule.

In another embodiment, the method comprises (a) preparing multiple nucleic acid molecules, wherein each nucleic acid molecule comprises (i) a protein-binding domain and (ii) a nucleic acid sequence encoding a fusion protein comprising a polypeptide of interest and a DNA-binding protein that binds the protein-binding domain, (b) contacting a substrate with the multiple nucleic acid molecules, wherein the substrate comprises multiple DNA-binding proteins and multiple nucleic acid sequences comprising the protein-binding domain, whereupon each of the multiple nucleic acid molecules is immobilized on the substrate via binding to a DNA-binding protein on the substrate, (c) contacting the immobilized nucleic acid molecules with an expression composition, wherein the nucleic acid sequence encoding the fusion protein is expressed and the fusion protein is produced, whereupon each fusion protein is immobilized on the substrate via binding to a nucleic acid sequence comprising the protein-binding domain on the substrate.

BRIEF DESCRIPTION OF THE SEVERAL VIEWS OF THE DRAWING(S)

DETAILED DESCRIPTION OF THE INVENTION

Figure 1:
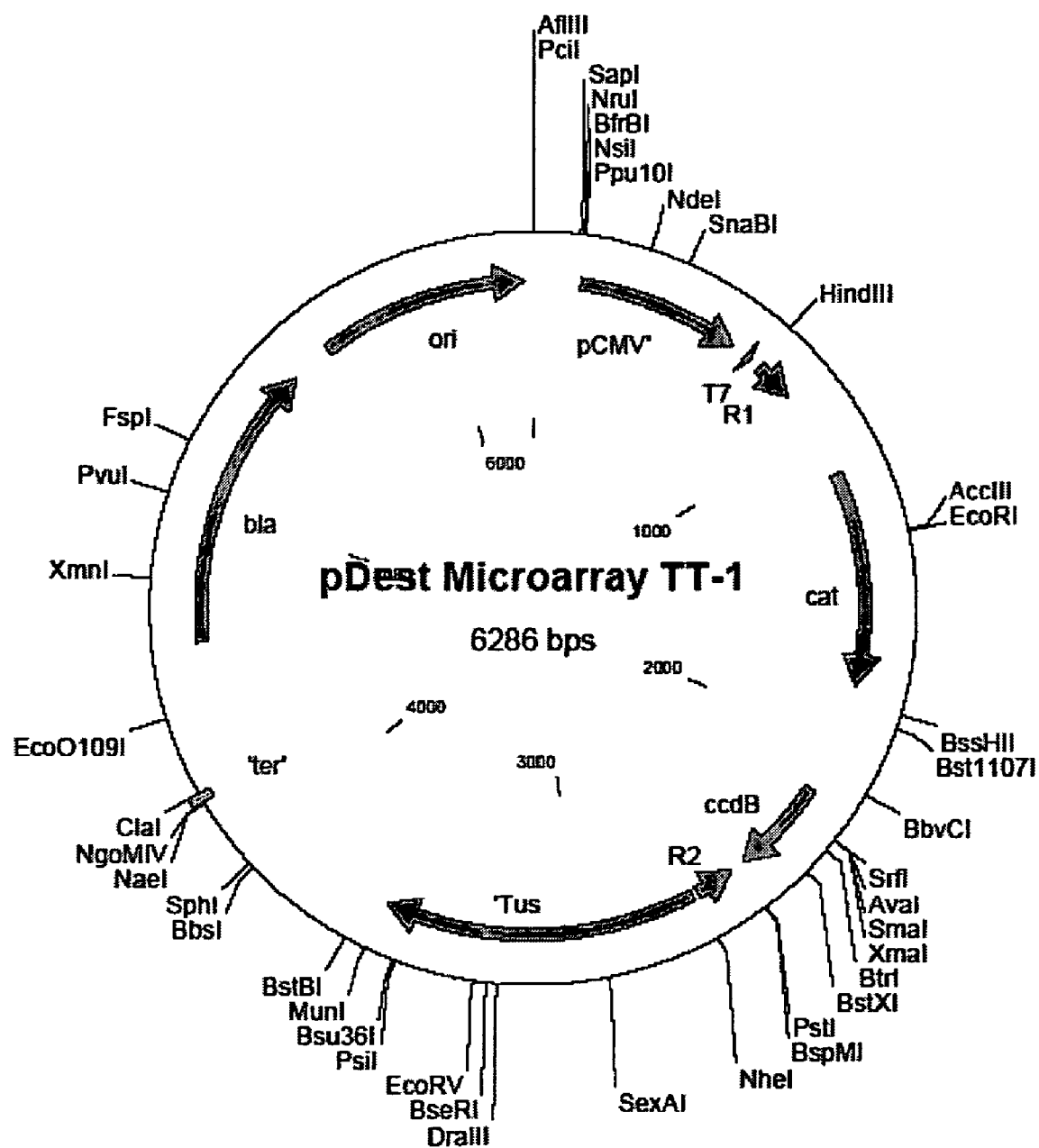
FIG. 1 is a diagram of the base vector pDest Microarray TT-1.

The invention provides a microarray. In an embodiment, the microarray comprises (a) a substrate, (b) multiple nucleic acid molecules immobilized on the substrate, wherein each nucleic acid molecule comprises (i) a protein-binding domain and (ii) a nucleic acid sequence encoding a fusion protein comprising a polypeptide of interest and a DNA-binding protein, and (c) one or more fusion proteins produced from the multiple nucleic acid molecules as a result of contacting the microarray with an expression composition, wherein each fusion protein is immobilized on the substrate via binding to the protein-binding domain on the nucleic acid molecule.

The invention also provides methods for producing protein microarrays. In one embodiment, the method comprises (a) preparing multiple nucleic acid molecules, wherein each nucleic acid molecule comprises (i) a protein-binding domain and (ii) a nucleic acid sequence encoding a fusion protein comprising a polypeptide of interest and a DNA-binding protein, (b) contacting a substrate with the multiple nucleic acid molecules, (c) immobilizing the multiple nucleic acid molecules on the substrate, and (d) contacting the immobilized nucleic acid molecules with an expression composition, wherein the nucleic acid sequence encoding the fusion protein is expressed and the fusion protein is produced, whereupon each fusion protein is immobilized on the substrate via binding to a protein-binding domain on the nucleic acid molecule.

In another embodiment, the method comprises (a) preparing multiple nucleic acid molecules, wherein each nucleic acid molecule comprises (i) a protein-binding domain and (ii) a nucleic acid sequence encoding a fusion protein comprising a polypeptide of interest and a DNA-binding protein, (b) contacting a substrate with the multiple nucleic acid molecules, wherein the substrate comprises multiple nucleic acid sequences comprising the protein-binding domain and multiple DNA binding proteins, whereupon each of the multiple nucleic acid molecules is immobilized on the substrate via binding to a DNA-binding protein on the substrate, and (c) contacting the immobilized nucleic acid molecules with an expression composition, wherein the nucleic acid sequence encoding the fusion protein is expressed and the fusion protein is produced, whereupon each fusion protein is immobilized on the substrate via binding to a nucleic acid sequence comprising a protein-binding domain on the substrate.

The inventive microarray and methods for producing protein microarrays comprises using or preparing multiple nucleic acid molecules, wherein each nucleic acid molecule comprises (i) a protein-binding domain and (ii) a nucleic acid sequence encoding a fusion protein comprising a polypeptide of interest and a DNA-binding protein. Each of the nucleic acid molecules can be any type of nucleic acid molecule, such as DNA, RNA, or cDNA. The multiple nucleic acid sequences can be of different types (e.g., a mixture of DNA and cDNA), but preferably they are of the same type. Desirably, each of the nucleic acid molecules is DNA, preferably supercoiled DNA, and most preferably supercoiled plasmid DNA. Any suitable number of nucleic acid sequences can be prepared. In that the inventive method can provide for high-throughput analysis of proteins, the invention typically comprises preparing at least 50 nucleic acid molecules (e.g., 50, 60, 70, 80, 90, or more nucleic acid molecules), preferably at least 100 nucleic acid molecules (e.g., 100, 200, 300, 400, or more nucleic acid molecules), and more preferably at least 500 nucleic acid molecules (e.g., 500, 600, 700, 800, 900, or more nucleic acid molecules). One of ordinary skill in the art will appreciate that the number of nucleic acid molecules prepared for use in the inventive array or method will depend upon the particular system or conditions used.

Each of the multiple nucleic acid molecules comprises a protein-binding domain. The term "protein-binding domain," as used herein, refers to any nucleic acid sequence that is capable of being recognized and bound by a protein or peptide. Each nucleic acid molecule comprises one or more protein-binding domains (e.g., 1 or more, 2 or more, 5 or more, or 10 or more protein-binding domains). The protein-binding domain can be any suitable prokaryotic or eukaryotic protein-binding domain known in the art. Examples of suitable protein-binding domains include, but are not limited to, homeobox responsive elements (HRE) and operator sequences. Protein-binding domains are further described in, for example, Alberts et al., eds., *Molecular Biology of the Cell*, 3$^{rd}$ edition, Garland Publishing, Inc., New York (1994).

In a preferred embodiment of the invention, the nucleic acid sequence comprising a protein-binding domain is selected from the group consisting of an *E. coli* Ter sequence, an *E. coli* lactose (lac) operon operator sequence, and an *E. coli* galactose (gal) operon operator sequence. Most preferably, the nucleic acid sequence comprises an *E. coli* Ter nucleic acid sequence. A "Ter nucleic acid sequence," as used herein, refers to any replication termination sequence from any source including those found in eukaryotic and prokaryotic organisms (including gram positive and gram negative microorganisms). A Ter nucleic acid sequence also includes any portion of a full-length Ter nucleic acid sequence that is recognized and bound by one or more Ter-binding proteins (e.g., replication terminator proteins or peptides). A portion of a Ter nucleic acid sequence comprises at least 5 nucleotides (e.g., 5, 6, 7, 8, 9, 10, or more nucleotides) of a full-length Ter nucleic acid sequence, but less than an entire Ter nucleic acid sequence. The Ter nucleic acid sequence can be double stranded or single stranded. The Ter nucleic acid sequence preferably is a wild-type Ter nucleic acid sequence, but can also be a mutated Ter nucleic acid sequence, so long as the mutated Ter nucleic acid sequence retains the ability to bind a Ter-binding protein. Mutant Ter nucleic acid sequences can be generated using standard mutagenesis techniques (e.g., to make deletions, substitutions, and/or insertions in the Ter sequence or by standard chemical synthesis techniques (e.g., oligonucleotide synthesis)). Functional domains and regions of Ter nucleic acid sequences necessary for proper function are described in, for example, Kamada et al., *Nature*, 383: 598-603 (1996) and Coskun-Ari and Hill, *J. Biol. Chem.*, 272: 26448-26456 (1997). As discussed above, the Ter nucleic acid sequence preferably is an *E. coli* Ter nucleic acid sequence. Particularly preferred *E. coli* Ter nucleic acid sequences include SEQ ID NO: 1, SEQ ID NO: 2, SEQ ID NO: 3, SEQ ID NO: 4, SEQ ID NO: 5, SEQ ID NO: 6, and SEQ ID NO: 7. Ter nucleic acid sequences are further described in U.S. Patent Application Publication No. 2003/0176644 A1.

Each of the multiple nucleic acid molecules also encodes a fusion protein. A ("fusion protein," as used herein, refers to a hybrid protein comprising polypeptide portions derived from two or more different proteins, and is synonymous with "chimeric protein." In the context of the invention, each of the multiple nucleic acid molecules encodes a fusion protein comprising a polypeptide of interest and a DNA-binding protein (as described above) (hereinafter referred to as "the fusion protein"). The polypeptide of interest can be any suitable polypeptide obtained from any suitable organism. In one embodiment, the polypeptide is an animal polypeptide. The polypeptide can be derived from any suitable animal. Suitable animals include, for example, protozoa, echinoderms (e.g., sea urchins), annelids (e.g., earthworms), nematodes (e.g., *C. elegans*), mollusks, arthropods (e.g., crustaceans), insects, birds, amphibians, reptiles, and mammals (e.g., primates and rodents). Preferably, the organism is a mammal, and most preferably the organism is a human. In one embodiment, the polypeptide of interest is a target for a therapeutic agent (i.e., a drug). In this regard, the polypeptide of interest is a target for a known therapeutic agent, such as those described in, for example, *Physician's Desk Reference*, Medical Economics Co., Inc., Montvale, N.J. (2004). Alternatively, the polypeptide of interest is not a target for a known drug, but is a target against which a new drug is developed.

The fusion protein also comprises a DNA-binding protein. The term "DNA-binding protein," as used herein, refers to any peptide, polypeptide, or protein that recognizes and binds to a nucleic acid sequence, preferably a DNA sequence. The DNA-binding protein can recognize and bind to a specific sequence of DNA, however, the DNA-binding protein need not be sequence-specific. One of ordinary skill in the art will appreciate that most DNA-binding proteins bind to DNA as homodimers or heterodimers and recognize DNA through one of a small number of structural motifs. Examples of such structural motifs include, for example, the helix-turn-helix motif, the homeodomain motif, the zinc finger motif, the leucine zipper motif, and the helix-loop-helix motif. The precise amino acid sequence that is folded into the binding motif determines the particular DNA sequence that is recognized by the DNA-binding protein. The DNA-binding protein can be any suitable eukaryotic or prokaryotic DNA-binding protein known in the art. Suitable DNA-binding proteins include, for example, TATA-box binding proteins, *E. coli* lacI protein, *E. coli* lac repressor protein (lacR), *E. coli* galactose operon repressor protein (GalR), eukaryotic transcription factor TFIIIA, bacteriophage lambda Cro protein, yeast GCN4 transcription activator, AP-1, and Ter-binding proteins (e.g., *E. coli* Tus protein). Artificial DNA binding proteins generated by methodologies known in the art (e.g., ribosome diplay, mRNA display, phage display, etc.) also can be used. Other DNA-binding proteins are described in, for example, Alberts et al, supra.

Preferably, the DNA-binding protein is a Ter-binding protein. A "Ter-binding protein" includes any protein that binds a Ter nucleic acid sequence. As discussed above, such proteins include, for example, replication terminator proteins (RTPs). An RTP is a sequence specific DNA-binding protein which, when bound to a double stranded Ter nucleic acid sequence, induces DNA replication arrest. In the context of the invention, the Ter-binding protein preferably is an *E. coli* Tus protein. The Tus protein (also referred to in the art as tau) is an RTP from *E. coli* with a molecular weight of 36,000 daltons (Da). The gene encoding Tus has been identified (see Hidaka, et al., *J. Biol. Chem.*, 264: 21031-21037 (1989) and Hill et al., *Proc. Natl. Acad. Sci. U.S.A.*, 86: 1593-1597 (1989)). The Tus protein binds Ter-sites as a monomer, and the crystal structure of the Tus-Ter complex has been elucidated (Bussiere, et al., *Molecular Microbiology*, 31(6): 1611-1618 (1999)). Tus binds the TerB site tightly with a dissociation constant of up to $3\times10^{-13}$ M in vitro (depending on the buffer conditions). The binding of Tus to other Ter-sites is somewhat less tight with dissociation constants on the order of $10^{-10}$ to $10^{-11}$ M. The Ter-binding protein employed in the fusion protein preferably has a dissociation constant from a Ter-site of about $10^{-9}$ M to about $10^{-15}$ M, more preferably from about $10^{-10}$ M to about $10^{-14}$ M, and most preferably from about $10^{-11}$ M to about $10^{-13}$ M.

While the fusion protein preferably comprises a wild type Tus protein, a fusion protein comprising a mutant or variant of the Tus protein which retains the ability to bind a Ter nucleic acid sequence is within the scope of the invention. Suitable mutants include those with mutations in the DNA-binding domain such as those disclosed in Skokotas et al., *J. Biol. Chem.*, 270: 30941-30948 (1995)). Functional domains of some Ter-binding proteins have been defined and may be altered to increase their ability to bind Ter. For example, mutations can be made in the replication fork-blocking domain of a Ter binding protein (see, e.g., Duggin et al, *J. Mol. Biol.*, 286: 1325-1335 (1999)).

The fusion protein can comprise a modified Ter-binding protein. The modified Ter-binding protein may be a full length Ter-binding protein or a fragment of a Ter-binding protein that retains the ability to bind a Ter nucleic acid sequence. The Ter-binding protein can be modified by covalently attaching a moiety to the Ter-binding protein. The moiety may be covalently attached to the Ter-binding protein, for example, through the use of coupling reagents known in the art, such as those commercially available from, for example, Pierce Chemical Co., Rockford, Ill. The modifying moiety can be any suitable moiety that can be covalently attached to the Ter-binding protein. Suitable moieties include, but are not limited to, peptides, carbohydrates, and polysaccharides. In addition, the moiety can be a detection molecule. Suitable detection molecules are known to those skilled in the art and include, but are not limited to, enzymes with detectable activities such as horseradish peroxidase, alkaline phosphatase, luciferase, beta-galactosidase and beta-glucuronidase, fluorescent moieties, chromophores, haptens and/or epitopes recognized by an antibody. In embodiments where the fusion protein comprises a fragment of a Ter-binding protein, the fragment can be of any size that is less than the full-length Ter-binding protein but which retains the ability to bind a Ter nucleic acid sequence with sufficient affinity. Fragments of a Ter binding protein can be assayed for their ability to bind a Ter sequence using routine methods known in the art, such as, for example, gel mobility shift assays and DNA footprinting assays.

The nucleic acid sequence encoding the fusion protein is operably linked to a promoter. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. Any promoter (i.e., whether isolated from nature or produced by recombinant DNA or synthetic techniques) can be used in connection with the invention to provide for transcription of the nucleic acid sequence encoding the fusion protein. The promoter preferably is capable of directing transcription in a eukaryotic or prokaryotic cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements")

in that enhancers can function in either orientation, and over distances of up to several kilobase pairs (kb), even from a position downstream of a transcribed region.

Promoter regions can vary in length and sequence and can further encompass one or more DNA binding sites for sequence-specific DNA binding proteins and/or an enhancer or silencer. Enhancers and/or silencers can similarly be present on a nucleic acid sequence outside of the promoter per se. Desirably, a cellular or viral enhancer, such as the cytomegalovirus (CMV) immediate-early enhancer, is positioned in the proximity of the promoter to enhance promoter activity. In addition, splice acceptor and donor sites can be present on a nucleic acid sequence to enhance transcription.

The nucleic acid sequence can be operably linked to a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.,* 78, 144-145 (1981)), promoters derived from SV40 or Epstein Barr virus, an adeno-associated viral promoter, such as the p5 promoter, and the like.

Alternatively, the invention employs a cellular promoter, i.e., a promoter that drives expression of a cellular protein. In this regard, the cellular promoter can be a constitutive promoter that works in a variety of cell types, and drives expression of genes encoding transcription factors, housekeeping genes, or structural genes common to eukaryotic cells. For example, the Ying Yang 1 (YY1) transcription factor (also referred to as NMP-1, NF-E1, and UCRBP) is a ubiquitous nuclear transcription factor that is an intrinsic component of the nuclear matrix (Guo et al., *PNAS,* 92: 10526-10530 (1995)). YY1 is a regulatory protein that responds to changes in the cellular environment. While the promoters described herein are considered as constitutive promoters, it is understood in the art that constitutive promoters can be upregulated. Promoter analysis shows that the elements critical for basal transcription reside from −277 to +475 of the YY1 gene relative to the transcription start site from the promoter, and include a TATA and CCAAT box. JEM-1 (also known as HGMW and BLZF-1) also is a ubiquitous nuclear transcription factor identified in normal and tumorous tissues (Tong et al., *Leukemia,* 12(11): 1733-1740 (1998), and Tong et al., *Genomics,* 69(3): 380-390 (2000)). JEM-1 is involved in cellular growth control and maturation, and can be upregulated by retinoic acids. Sequences responsible for maximal activity of the JEM-1 promoter haves been located at −432 to +101 of the JEM-1 gene relative the transcription start site of the promoter. Unlike the YY1 promoter, the JEM-1 promoter does not comprise a TATA box. The ubiquitin promoter, specifically UbC, is a strong constitutively active promoter functional in several species. The UbC promoter is further characterized in Marinovic et al., *J. Biol. Chem.,* 277 (19): 16673-16681 (2002).

Many of the above-described promoters are constitutive promoters. Instead of being a constitutive promoter, the promoter can be an inducible promoter, i.e., a promoter that is up and/or down-regulated in response to appropriate signals. Examples of suitable inducible promoter systems include, but are not limited to, the IL-8 promoter, the metallothionine inducible promoter system, the bacterial lacZYA expression system, and the tetracycline expression system. The promoter sequence that regulates expression of the nucleic acid sequence can contain at least one heterologous regulatory sequence responsive to regulation by an exogenous agent. The regulatory sequences are preferably responsive to exogenous agents such as, but not limited to, drugs, hormones, or other gene products.

Preferably, the promoter is a bacteriophage promoter. Suitable bacteriophage promoters include, for example, a phage T3 promoter, a phage T7 promoter, a phage M13 promoter, a phage SP6 promoter, and a hybrid phage T5 promoter. Most preferably, the promoter is a phage T7 promoter.

The construction of fusion proteins is routine in the art (see, e.g., U.S. Pat. Nos. 5,130,247 and 6,254,870). The polypeptide of interest may be fused to the N-terminal of the DNA-binding protein, the C-terminal of the DNA-binding protein or at an interior position of the DNA-binding protein. Any site of fusion may be used so long as the binding capability of the DNA-binding protein is not substantially reduced. In this context, substantially reduced indicates that the DNA-binding protein does not bind a protein binding domain with sufficient affinity to allow immobilization and detection of the fusion protein comprising a DNA-binding protein.

The invention further comprises a substrate which is contacted with the multiple nucleic acid molecules. Substrates for use in the invention can be any support or matrix suitable for attaching nucleic acid molecules and proteins. Suitable substrates include, but are not limited to, silicon, nitrocellulose, diazocellulose, glass, polystyrene (including microtitre plates), polyvinylchloride, polypropylene, polyethylene, polyvinylidenedifluoride (PVDF), dextran, sepharose, agar, starch, nylon, and metal. The substrate can be in any form or configuration, including chips, plates, beads, filters, membranes, sheets, frits, plugs, columns, and the like. The substrate can also include multi-well tubes or plates, such as 12-well plates, 24-well plates, 48-well plates, 96-well plates, and 384-well plates. Preferred beads are made of glass, latex, or a magnetic material (magnetic, paramagnetic, or superparamagnetic beads).

In one embodiment of the invention, the multiple nucleic acid molecules encoding the fusion proteins are immobilized directly on the substrate using routine methods known in the art. In another embodiment of the invention, the substrate comprises multiple DNA-binding proteins and multiple nucleic acid sequences comprising a protein-binding domain. In this embodiment, the DNA-binding protein on the substrate binds to the protein-binding domain present in each fusion protein-encoding nucleic acid molecule. Nucleic acid molecules can be applied, printed, or spotted onto the substrate using photolithography, pipetting, drop-touch methods, piezoelectric (ink-jet) methods, electric methods, robotic methods, and other methods known in the art. Nucleic acid molecules can be immobilized on a particular substrate by noncovalent or covalent interactions. In this regard, nucleic acid sequences can be noncovalently immobilized on a glass slide coated with, for example, either poly-L-lysine or aminopropyltri-ethoxysilane. The noncovalent charge interactions between the negatively charged phophodiester groups of the nucleic acids and the positively charged amino groups of, for example, surface-bound lysine side-chains, can result in decreased sensitivity of the microarray due to loss of nucleic acids from the glass surface. Thus, the nucleic acid molecules preferably are immobilized on the substrate via covalent interactions. Methods for covalently immobilizing nucleic acids onto various microarray substrates are described in, for example, Beaucage, *Curr. Medicinal Chem.,* 8: 1213-1244 (2001). DNA microarray fabrication, immobilization, and analysis are further described in, for example, Schena, ed., *Microarray Biochip Technology,* Eaton Publishing Company/Biotechniques Books, 298 pp. (2000). Proteins can be applied, printed, or spotted onto the substrate using, for example, piezoelectric dispensing methods, robotic methods, contact-pin printing technology, and other methods known in the art. Like nucleic acids, proteins can be immobilized on a substrate via noncovalent or covalent interactions, but covalent interactions preferably are used. In this regard, for example, proteins can be spotted on glass slides coated with aminosilane, poly-L-lysine, or agarose film, and immobilized on the slides by the Schiff base aldehyde-amine chemistry. Protein microarray fabrication, immobilization, and analysis are further described in, for example, Schena, ed., *Protein Microarrays*, Jones and Bartlett Publishers, Inc., 496 pp. (2004), MacBeath, *Nature Genetics*, 32: 526-532 (2002), MacBeath et al., *Science,* 289: 1760-1763 (2000), and Tang et al., *Advanced Nanomaterials and Nanodevices, 8th International Conference on Electronic Materials*, Xi'an, China, Jun. 10-14 (2002)).

The invention further comprises contacting the immobilized nucleic acid molecules with an expression composition, wherein the nucleic acid sequence encoding the fusion protein is expressed and the fusion protein is produced. The term "expression composition," as used herein, refers to a composition comprising all of the elements required for transcription and translation of a nucleic acid sequence. Such elements are known in the art and include, for example, RNA polymerase, transcription factors, splicing factors, tRNA molecules, etc. The expression composition can be any suitable composition that enables cell-free transcription and translation. The expression composition preferably comprises the transcription and translation machinery of rabbit reticulocytes, wheat germ extract, *E. coli*, or any other suitable source. Rabbit reticulocytes can translate large MRNA transcripts and carry out post-translational processing, such as glycosylation, phosphorylation, acetylation, and proteolysis. Wheat germ extract is best suited for expression of smaller proteins, and *E. coli* cell-free extracts are capable of carrying out transcription and translation in the same reaction environment. Commercially available cell-free expression compositions include, for example, rabbit reticulocyte extracts (Promega, Madison, Wis.), pCOLADuet™ (Novagen, Madison, Wis.), Expressway™ Linear Expression System (Invitrogen Corp., Carlsbad, Calif.), pIEX™ Insect Cell Expression Plasmids (Novagen, Madison, Wis.) and the Rapid Translation System (Roche Diagnostics Corp., Indianapolis, Ind.).

Figure 3:
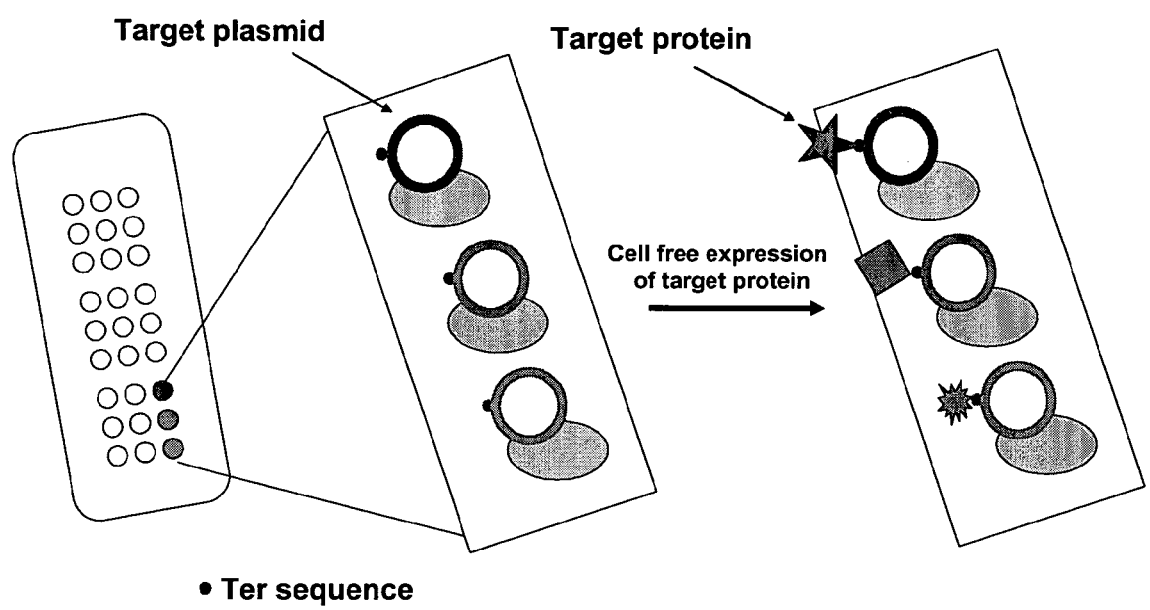
FIG. 3 is a diagram illustrating a protein microarray in which Tus fusion proteins are captured by a Ter sequence in the plasmid encoding the Tus fusion protein.
Figure 4:
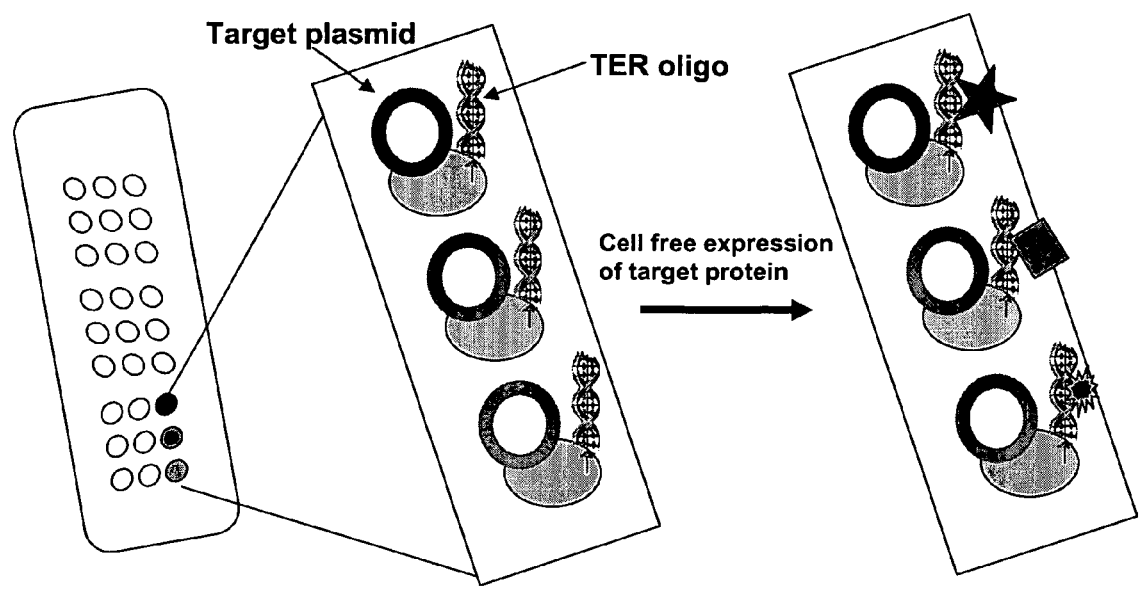
FIG. 4 is a diagram illustrating a protein microarray in which Tus fusion proteins are captured by a Ter sequence present in the oligonucleotides on the microarray.

Upon transcription of the multiple nucleic acid sequences and translation of the encoded fusion proteins, each fusion protein is immobilized on the substrate via interaction of the DNA-binding protein portion of the fusion protein with a nucleic acid sequence comprising a protein-binding domain. In embodiments where the multiple nucleic acid molecules encoding the fusion proteins are immobilized directly on the substrate, the fusion proteins are immobilized on the substrate via binding to the protein-binding domain present on the nucleic acid molecules from which the fusion proteins are produced. For example, plasmids comprising a Ter nucleic acid sequence and encoding a fusion protein comprising a polypeptide of interest and a Tus protein can be spotted on a substrate and subjected to cell-free transcription/translation. The resulting fusion protein is immobilized on the substrate by binding to the Ter nucleic acid sequence on the plasmid (see FIG. 3). One of ordinary skill in the art will appreciate that this example is equally applicable to other DNA-binding proteins and protein binding domains disclosed herein. Alternatively, in embodiments where the substrate comprises multiple nucleic acid sequences comprising the protein-binding domain, the fusion proteins are immobilized on the substrate via the DNA-binding protein portion of the fusion protein binding to a protein-binding domain on the substrate (see, e.g., FIG. 4).

The invention further provides a method of analyzing interactions between a protein and a compound of interest. The method comprises (a) producing a protein microarray as described herein, (b) contacting the protein microarray with a sample comprising one or more compounds of interest, and (c) detecting binding of the one or more compounds of interest with one or more of the fusion proteins immobilized on the protein microarray. Descriptions of the protein microarray, the DNA-binding protein, the protein-binding domain, and the nucleic acid molecules encoding a fusion protein set forth above in connection with other embodiments of the invention also are applicable to those same aspects of the aforesaid inventive method for analyzing protein-protein interactions.

It will be appreciated that the method for analyzing interactions between a protein and a compound of interest is used to identify compounds that interact with the polypeptide of interest present in the fusion protein immobilized on the substrate. In this manner, the inventive method can be employed to elucidate potential drug targets, and to map particular biological pathways. Thus, the compound of interest can be any compound that interacts with a protein, including, but not limited to, other proteins, nucleic acid molecules, lipids, and drugs. The sample comprising one or more compounds of interest can be any suitable sample, but preferably is a sample obtained from a mammal (e.g., a human). The sample can be a solid sample, such as a tissue sample, or the sample can be fluid, such as a sample of body fluid. For instance, a section of whole tissue can be homogenized to liquefy the components found in the tissue. The tissue sample can be obtained from any suitable organ, including diseased organs (e.g., organs affected by cancer). Suitable fluid samples include, but are not limited to, blood, saliva, serum, plasma, lymph, interstitial fluid, and cerebrospinal fluid.

Whatever sample is used, each of the one or more compounds in the sample preferably comprises a detectable label. The detectable label preferably is attached to each protein via covalent linkage to the amino groups on the proteins. Any suitable detectable label known in the art can be employed in the inventive method. Preferably, the detectable label is a fluorescent dye, such as, for example, Cy5 (red fluorescence) and Cy3 (green fluorescence). The sample preferably is in a solution, and is applied to the protein microarray using methods described in the art. Methods for preparing protein samples for protein microarrays are described in, for example, Haab et al., supra.

Once the sample has been applied to the protein microarray, the microarray is incubated under conditions that allow for compounds in the sample to bind one or more fusion proteins on the microarray. Incubation conditions will vary depending on the type of compounds analyzed and the detectable labels employed. Detection schemes are generally described in, for example, Haab et al., supra, MacBeath et al., supra, and Kodadek, *Chemistry & Biology,* 8: 105-115 (2001)). Typically and preferably, all unbound compounds are washed off the microarray, leaving only bound compounds. The binding of a compound in the sample to a fusion protein on the microarray preferably is visualized via fluorescence detection. To maximize the robustness and quantitative accuracy of the microarray, comparative fluorescence measurements can be made, using an internal standard for each protein to be assayed. In this respect, two differentially labeled solutions containing compounds of interest can be mixed together and then incubated with the microarray so that the fluorescence ratio at each spot on the microarray corresponds to the ratio of each compound in the two solutions (see, e.g., Haab et al., supra).

The following examples further illustrate the invention but, of course, should not be construed as in any way limiting its scope.

EXAMPLE

This example demonstrates the production of a protein microarray in accordance with the invention.

Construction of Base Microarray Plasmid

A base microarray plasmid vector (pDest Microarray TT-1) containing a Ter site and a Tus protein for cloning genes of interest was constructed. First, a destination vector was made with *E. coli* Tus protein as a carboxy fusion partner. A Tus protein with greater affinity for a Ter sequence (Tus E47Q) was amplified from plasmid DNA by standard procedures (see Henderson et al., *Mol. Genet. Genomics*, 265: 941-953 (2001)). The sequences of the oligonucleotides used for the Tus amplifications are set forth below as SEQ ID NO: 8 and SEQ ID NO: 9. Restriction sites NheI and MunI are indicated as bold and underlined. A six-histidine tag (underlined and italics) was incorporated in the reverse primer so to enable downstream identification of Tus.

```
Forward-
                                        (SEQ ID NO: 8)
5'-ATTTTAGCT AGCGGAGGTGCGCGTTACGATCTCGTAGACCGAC

TC-3'

Reverse
                                        (SEQ ID NO: 9)
5'-TATATTCAATTGTTAATGATGGTGATGATGGTGATCTGCAACAT

ACAGGTGCAGCCGTGG 3'.
```

The PCR product was purified and digested with NheI and MunI, and run on an agarose gel. The fragment was purified again and cloned into a derivative pDest47 vector (Invitrogen Corp., Carlsbad, Calif.), called pDest472, and digested to create pDest 472-Tus. Correct clones were selected by restriction digestion and by sequencing.

A Ter site (bold and underlined) was synthesized by annealing two complementary oligos having the following sequences:

```
                                       (SEQ ID NO: 10)
CCGGCCACTTTAGTTACAACATACTTATTAT
and (SEQ ID NO: 11)
CGATAATAAGTATGTTGTAACTAAAGTGG
```

Upon annealing, the complementary oligonucleotides formed a double stranded Ter site with ClaI and NgoMIV digested overhangs. The annealed oligonucleotide was cloned into pDest 472-Tus digested with NgoMIV and ClaI to create pDest Microarray TT-1 (see FIG. 1). The clone was verified by sequencing. As stated above, this base plasmid is suitable for constructing an in-frame Tus fusion with any protein of interest using the Gateway™ recombinational cloning system (Invitrogen Corp., Carlsbad, Calif.).

In addition to a wild-type Ter site, a mutant Ter site was also tested for Tus fusion capture. During the course of cloning the Ter site above, a mutant Ter site was obtained. The mutated Ter site has the following sequence (the mutation site is underlined) CACTTTAGTTACAACATATTTATT (SEQ ID NO: 12). It has been shown that mutation at this particular site reduces the Tus binding affinity by almost 4-fold (see Coskun-Ari et al., supra).

Construction of GFP Fusion Plasmid

Figure 2:
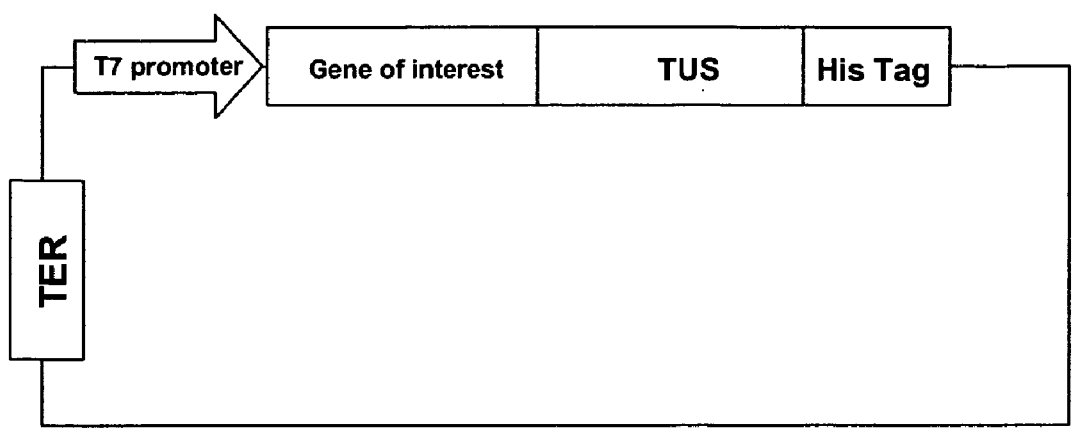
FIG. 2 is a diagram of a plasmid vector comprising a Ter sequence and a nucleic acid sequence encoding a fusion protein comprising a polypeptide of interest and a Tus protein.

Green fluorescent protein (GFP) was cloned as a fusion with the Tus protein. The plasmid pEL100 contains a GFP gene inserted into pDonr223 (Invitrogen Corp., Carlsbad, Calif.). The vector pEL100 contains a Kozak sequence upstream of ATG and no stop codon at the C-terminus. Thus, upon recombinational cloning into pDest Microarray TT-1, GFP was in frame with Tus (GFP-Tus-His6 plasmid) (see FIG. 2). Recombinational cloning using the Gateway™ system (Invitrogen Corp., Carlsbad, Calif.) was performed as per the manufacturer's instructions. The clone was sequenced to confirm proper insertion. To demonstrate the specificity of Tus-Ter binding, a GFP-Tus-His6 plasmid lacking a Ter site also was tested.

Microarray Fabrication

GFP-Tus-His6 plasmids were prepared in 3× standard saline citrate (SSC) in a 384-well plate (Genetix USA, Inc., Boston, Mass.) and arrayed on FAST™ nitrocellulose coated slides (Schleicher & Schuell BioScience, Keene, N.H.) using a Microgrid II arrayer at 50% humidity. After printing the FAST™ slides with the GFP-Tus-His6 plasmids, they were baked at 80° C. for 30 minutes. Slides were blocked with 0.1% PVP/0.05% Tween 20 for 1 hour prior to expression.

In situ Protein Expression

In situ expression was performed using a cell-free expression system (TNT Quick coupled transcription/translation system (Promega Corp., Madison, Wis.)). Briefly, 30 µl of rabbit reticulocyte lysate supplemented with methionine, according to manufacturer's instructions, was added directly to the slide. Expression and immobilization were carried out at 30° C. for 1.5 hours followed by incubation at 15° C. for 2 hours in a water bath.

Confirmation of Expression and Immobilization of Expressed Proteins

Expression of the GFP-Tus fusion protein was confirmed with Cy3 and Cy5 labeled monoclonal antibodies to the His6 (poly-his) tag. Prior to incubation with the labeled antibody, slides were blocked for 1 hour with 0.1% PVP/0.05% Tween 20. The monoclonal antibody to the poly-his tag (Sigma-Aldrich, St. Louis, Mo.) was labeled with fluorescent dye N-hydroxysuccinimide (NHS) ester-linked Cyanine 3 (Cy3) and Cyanine 5 (Cy5) (Amersham BioSciences, Piscataway, N.J.). Briefly, 90 µl of the anti-poly-his antibody diluted to the concentration of 0.55 mg/ml in 0.1 M sodium bicarbonate/carbonate buffer pH 9.0 was mixed with 20 µl of 60 µM of Cy3 or Cy5 in sodium bicarbonate/carbonate buffer and incubated on ice. After the reaction had proceeded for 90 minutes, 8 µl of Blocking Buffer (BD Biosciences, San Jose, Calif.) was added to the solution to quench the reactions, and the solutions were allowed to sit for another 30 minutes with additional mixing approximately every 10 minutes. The unconjugated dye was removed by passing each sample through a size-exclusion chromatography spin column (sephadex G-15 (Sigma Aldrich, St. Louis, Mo.) in Micro Bio-spin columns (Bio-Rad Laboratories, Inc., Hercules, Calif.). Molar concentrations for labeled protein and dye were calculated. The Cy5-labeled anti-his antibody was mixed with an equal amount of the Cy3-labeled anti-his antibody and diluted in the array buffer (0.1% PVP/0.05% Tween 20). Hybridization to the array was performed in an incubation chamber at 4° C. with gentle rocking for at least 12 hours. After incubation, slides were washed three times for 5 minutes each in 10 mM PBS/0.05% Tween 20, followed by one wash in 10 mM PBS for one minute. All washes were performed at 4° C. Slides were dried and subjected to fluorescence detection.

The hybridized arrays were scanned with an Axon GenePix 4000 scanner (Molecular Devices Corporation, Sunnyvale, Calif.), and fluorescence data were collected and evaluated with the GenePix Pro 5.0 software (Molecular Devices Corporation, Sunnyvale, Calif.). For the microarray imaging, the Axon GenePix 4000 scanner was set at 100% laser power and 350% PMT gain.

Significant signal intensities (see Table 1, arbitrary units of 14000 and 20574 with Cy5 and Cy3, respectively) were observed from the array containing the vector with a wild type Ter site, confirming the expression and binding of the GFP-Tus fusion protein. On the other hand, no signal intensity was observed in Cy5 and a faint signal was observed in Cy3 (2463 units) from the array containing the vector without any Ter site. The signal ratio of TER−/TER+(no mutation; wild-type) was 0 for Cy5 and 0.12 for Cy3. These numbers represent higher binding of labeled anti-his antibody to the fusion protein expressed from the plasmid with wild-type Ter (no mutation) when compared with the control plasmid without any Ter site (no TER), and suggest that no binding occurred between the fusion protein and the plasmid without any Ter site.

To determine whether a mutation in the Ter sequence could influence the formation of the Tus-Ter binding complex and affect microarray fabrication, the hybridization signal from the wild-type Ter vector was compared with the hybridization signal from the mutated Ter (Mut) vector described above. The results of these experiments are set forth below in Table 1.

TABLE 1

| Plasmid | Cy5 Signal Intensity (Background subtracted) | Cy3 Signal Intensity (Background subtracted) |
| --- | --- | --- |
| +TER (wild type) | 14000 | 20574 |
| +TER (mutant) | 4738 | 10920 |
| −TER | 0 | 2463 |

The signal ratio of TER(−)/mutant TER(+) was 0 for Cy5 and 0.22 for Cy3.

These data confirm the expression and binding of the GFP-Tus fusion protein to the vector comprising a mutated Ter site. This vector, however, produced lower signal intensities than those observed with the vector comprising a wild-type Ter site. These results demonstrate that an intact Ter sequence is necessary for Tus binding, which in turn enables the binding of the expressed fused protein to the vector immobilized on the microarray slide.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and ("containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A microarray comprising:
   (a) a substrate;
   (b) multiple nucleic acid molecules immobilized on the substrate, wherein each nucleic acid molecule comprises (i) one or more E. coli Ter sequences and (ii) a nucleic acid sequence encoding a fusion protein comprising a polypeptide of interest and an E. coli Tus protein; and
   (c) one or more fusion proteins produced from each of the multiple nucleic acid molecules of (b), wherein at least one or more of the fusion proteins produced by each of the multiple nucleic acid molecules in (b) are immobilized on the substrate via binding to the one or more Ter sequences, and wherein said Ter sequences are located outside the nucleic acid sequence which encodes the fusion protein of (b)(ii).

2. The microarray of claim 1, wherein the substrate is selected from the group consisting of silicon, nitrocellulose, diazocellulose, glass, polystyrene, polyvinylchloride, polypropylene, polyethylene, polyvinylidenedifluoride, dextran, sepharose, agar, starch, nylon, and metal.

3. The microarray of claim 1, wherein each of the multiple nucleic acid molecules is a plasmid.

4. The microarray of claim 1, wherein each of the multiple nucleic acid molecules is supercoiled.

5. The microarray of claim 1, wherein the nucleic acid sequence encoding the fusion protein is operably linked to a phage T7 promoter.

6. A method for producing a protein microarray, which method comprises:
   (a) preparing multiple nucleic acid molecules, wherein each nucleic acid molecule comprises (i) at least one or more E. coli Ter sequences and (ii) a nucleic acid sequence encoding a fusion protein comprising a polypeptide of interest and an E. coli Tus protein;
   (b) contacting a substrate with the multiple nucleic acid molecules of (a);
   (c) immobilizing the multiple nucleic acid molecules of (a) on the substrate; and
   (d) contacting the immobilized nucleic acid molecules of (a) with an expression composition, wherein the multiple nucleic acid molecules of (a) encoding the fusion protein are expressed and the fusion proteins are produced, whereupon at least one or more fusion proteins are immobilized on the substrate via binding to the at least one or more Ter sequences which are located outside the nucleic acid sequence which encodes the fusion protein of (a)(ii).

7. The method of claim 6, wherein the substrate is selected from the group consisting of silicon, nitrocellulose, diazocellulose, glass, polystyrene, polyvinylchloride, polypropylene, polyethylene, polyvinylidenedifluoride, dextran, sepharose, agar, starch, nylon, and metal.

8. The method of claim 6, wherein each of the multiple nucleic acid molecules is a plasmid.

9. The method of claim 6, wherein each of the multiple nucleic acid molecules is supercoiled.

10. The method of claim 6, wherein the nucleic acid sequence encoding the fusion protein is operably linked to a phage T7 promoter.

11. A method of analyzing interactions between a protein and compound of interest, which method comprises:
    (a) producing a protein microarray according to the method of claim 6;
    (b) contacting the protein microarray with a sample comprising one or more compounds of interest; and
    (c) detecting binding of the one or more compounds of interest with one or more of the fusion proteins immobilized on the protein microarray.

12. The method of claim 11, wherein the compound of interest is selected from the group consisting of a protein, a nucleic acid molecule, a lipid, and a drug.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Escherichia coli

<400> SEQUENCE: 1
aattagtatg ttgtaactaa agt                                              23

<210> SEQ ID NO 2
<211> LENGTH: 23
<212> TYPE: DNA
<213> ORGANISM: Escherichia coli -continued

```
<400> SEQUENCE: 2
aataagtatg ttgtaactaa agt                                        23

<210> SEQ ID NO 3
<211> LENGTH: 23
<212> TYPE: DNA
<213> ORGANISM: Escherichia coli

<400> SEQUENCE: 3
atataggatg ttgtaactaa tat                                        23

<210> SEQ ID NO 4
<211> LENGTH: 23
<212> TYPE: DNA
<213> ORGANISM: Escherichia coli

<400> SEQUENCE: 4
cattagtatg ttgtaactaa atg                                        23

<210> SEQ ID NO 5
<211> LENGTH: 21
<212> TYPE: DNA
<213> ORGANISM: Escherichia coli

<400> SEQUENCE: 5
ttaaagtatg ttgtaactaa g                                          21

<210> SEQ ID NO 6
<211> LENGTH: 23
<212> TYPE: DNA
<213> ORGANISM: Escherichia coli

<400> SEQUENCE: 6
ccttcgtatg ttgtaacgac gat                                        23

<210> SEQ ID NO 7
<211> LENGTH: 23
<212> TYPE: DNA
<213> ORGANISM: Escherichia coli

<400> SEQUENCE: 7
gatgagtatg ttgtaactaa cta                                        23

<210> SEQ ID NO 8
<211> LENGTH: 45
<212> TYPE: DNA
<213> ORGANISM: Artificial
<220> FEATURE:
<223> OTHER INFORMATION: Synthetic

<400> SEQUENCE: 8
attttagcta gcggaggtgc gcgttacgat ctcgtagacc gactc                45

<210> SEQ ID NO 9
<211> LENGTH: 59
<212> TYPE: DNA
<213> ORGANISM: Artificial
<220> FEATURE:
<223> OTHER INFORMATION: Synthetic

<400> SEQUENCE: 9
tatattcaat tgttaatgat ggtgatgatg gtgatctgca acatacaggt gcagcctgg  59

<210> SEQ ID NO 10
```

```
<211> LENGTH: 31
<212> TYPE: DNA
<213> ORGANISM: Artificial
<220> FEATURE:
<223> OTHER INFORMATION: Synthetic

<400> SEQUENCE: 10
ccggccactt tagttacaac atacttatta t                                          31

<210> SEQ ID NO 11
<211> LENGTH: 29
<212> TYPE: DNA
<213> ORGANISM: Artificial
<220> FEATURE:
<223> OTHER INFORMATION: Synthetic

<400> SEQUENCE: 11
cgataataag tatgttgtaa ctaaagtgg                                             29

<210> SEQ ID NO 12
<211> LENGTH: 24
<212> TYPE: DNA
<213> ORGANISM: Escherichia coli

<400> SEQUENCE: 12
cactttagtt acaacatatt tatt                                                  24
```